United States Patent [19]

Ozaki et al.

[11] Patent Number: 5,310,904
[45] Date of Patent: May 10, 1994

[54] PROCESS FOR PREPARING OPTICALLY ACTIVE BENZOTHIAZEPINE COMPOUNDS BY ASYMMETRIC REDUCTION

[75] Inventors: Yasuhiko Ozaki, Osaka; Shinichi Yamada, Hyogo; Hiroyasu Seko, Nara, all of Japan

[73] Assignee: Tanabe Seiyaku Co., Ltd., Osaka, Japan

[21] Appl. No.: 2,052

[22] Filed: Jan. 8, 1993

[30] Foreign Application Priority Data

Jan. 10, 1992 [JP] Japan .................................. 4-40040
Jun. 25, 1992 [JP] Japan .................................. 4-209402

[51] Int. Cl.$^5$ ........................................ C07D 281/02
[52] U.S. Cl. ............................................... 540/491
[58] Field of Search ...................................... 540/491

[56] References Cited

U.S. PATENT DOCUMENTS 5,128,469 7/1992 Nishimoto et al. ................ 540/491
5,223,612 7/1993 Giordano et al. ................... 540/491

FOREIGN PATENT DOCUMENTS 59-020273 2/1984 Japan ........................ C07D 281/10
60-032779 2/1985 Japan ........................ C07D 281/10

OTHER PUBLICATIONS

N. Umino et al., *Chem. Pharm. Bull.*, 27(6), 1479–1481 (1979).
M. F. Grundon et al., *Tetrahedron Letters*, No. 4, 295–296 (1976).
Y. Ohgo et al., *Chem. Abstr.* 72, 121886p (1970); corresponding to *Chem. Pharm Bull.*, 43(2), 505–509 (1970).
K. Soai et al., *Chem. Abstr.* 107, 197713s (1987); corresponding to *Chem. Lett.*, No. 11, 1897–1900 (1986).
Inoue et al., *Chem. Abstr.* 90, 6431w (1979); corresponding to Japanese Patent Second Publication No. 18038/1978.
Maeda et al., *Chem. Abstr.* 101, 38486e (1984); corresponding to Japanese Patent First Publication No. 20273/1984.
Giordano et al., *Chem. Abstr.* 115, 159190b (1991); corresponding to Japanese Patent First Publication No. 193770/1991.
Iwakuma et al., *Chem. Abstr.* 90, 6073f (1979); corresponding to Japanese Patent First Publication No. 105401/1978.
Morimoto et al., "Synthesis of 2-Substituted Derivatives of Diltiazem," *Heterocycles*, 30(1), 471–486 (1990).

*Primary Examiner*—Nicholas S. Rizzo
*Attorney, Agent, or Firm*—Finnegan, Henderson Farabow, Garrett & Dunner

[57] ABSTRACT

Process for preparing optically active cis-3-hydroxy-2,3-dihydro-1,5-benzothiazepin-4(5H)-one compounds [I] of the formula:

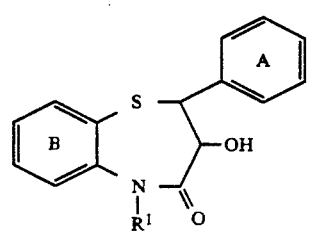

[I]

wherein Ring A and Ring B are substituted or unsubstituted benzene, R$^1$ is hydrogen or di-lower alkylaminoalkyl, which comprises subjecting 1,5-benzothiazepin-4(5H)-one (II) of the formula [II]:

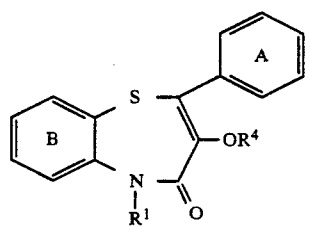

[II]

wherein R$^4$ is hydrogen or lower alkanoyl, and the other symbols are the same as defined above, to asymmetric reduction with a reaction product of optically active α-amino acid and metal hydride, in high optically yield, and said compounds [I] are very important as intermediate for preparing various medicines.

9 Claims, No Drawings

PROCESS FOR PREPARING OPTICALLY ACTIVE BENZOTHIAZEPINE COMPOUNDS BY ASYMMETRIC REDUCTION

The present invention relates to a novel process for preparing optically active benzothiazepine compounds by asymmetric reduction, more particularly, it relates to a novel process for preparing optically active cis-3-hydroxy-2-phenyl-2,3-dihydro-1,5-benzothiazepin-4(5H)-one compounds.

PRIOR ART

The desired compounds of the present invention, optically active cis-3-hydroxy-2-phenyl-2,3-dihydro-1,5-benzothiazepin-4(5H)-one compounds are very important as an intermediate for preparing diltiazem hydrochloride, which is useful as a coronary vasodilator, or other various medicines.

3-Hydroxy-2-phenyl-2,3-dihydro-1,5-benzothiazepin-4(5H)-one compounds exist in the form of four stereoisomers due to two asymmetric carbon atoms at 2- and 3-positions thereof. These four stereoisomers have different pharmaceutical activities, for instance, it has been known that although 2-(p-alkoxyphenyl)-3-acyloxy-5-(ω-dialkylaminoalkyl)-2,3-dihydro-1,5-benzothiazepin-4(5H)-ones show coronary vasodilating activity and brain wave stimulating activity, among four isomers thereof, the trans-compounds, i.e. (2S,3R)- and (2R,3S)-compounds, have weak pharmaceutical activities, and among the cis-compounds, the (2S,3S)-compounds show potent coronary vasodilating activity, and the (2R,3R)-compounds show brain wave stimulating activity (cf. Japanese Patent Second Publication (Kokoku) No. 18038/1978).

Accordingly, it is desired to obtain selectively a specific isomer having desired pharmaceutical activities. The above mentioned Japanese Patent Second Publication (Kokoku) No. 18038/1978 discloses processes for preparing optically active benzothiazepine derivatives, which comprise subjecting the intermediate, i.e. a racemic threo-2-hydroxy-3-(p-alkoxyphenyl)-3-(o-nitrophenylthio)propionic acid, to optical resolution with an optically active organic base such as cinchonidine, ephedrine and kinin.

Moreover, Japanese Patent First Publication (Kokai) No. 20273/1984 and Japanese Patent First Publication (Kokai) No. 193770/1991 disclose processes for preparing racemic 3-hydroxybenzothiazepine derivatives by reduction of 5-(2-dimethyl-aminoethyl)-substituted or unsubstituted 2-(4-methoxy-phenyl)-1,5-benzothiazepine-3,4(2H,5H)-dione compounds with a borohydride compound, respectively.

However, the above mentioned processes are still unsatisfactory, for example, in the low yield of desired optically active compounds from racemic synthetic intermediates, only 50% at most. Besides, these processes need complicated steps such as recovering unnecessary optically active compounds, or re-racemization in order to utilize the intermediate in full.

SUMMARY DESCRIPTION OF THE INVENTION

An object of the present invention is to provide a novel process for preparing desired optically active cis-3-hydroxy-2-phenyl-2,3-dihydro-1 5-benzothiazepin-4(5H)-one compounds selectively.

DETAILED DESCRIPTION OF THE INVENTION

According to the present invention, optically active cis-3-hydroxy-2-phenyl-2,3-dihydro-1,5-benzothiazepin-4(5H)-one compounds of the formula [I]:

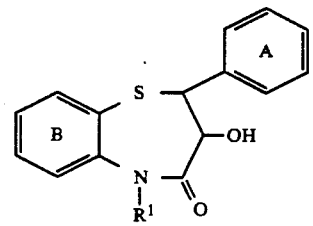

wherein Ring A and Ring B are a substituted or unsubstituted benzene ring, $R^1$ is hydrogen atom or a group of the formula:

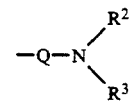

wherein $R^2$ and $R^3$ are the same or different and a lower alkyl group or a lower alkoxy-substituted phenyl-lower alkyl group, and Q is a lower alkylene group, can be stereoselectively prepared by asymmetric reduction of a 2-phenyl-1,5-benzothiazepin-4(5H)-one compound of the formula [II]:

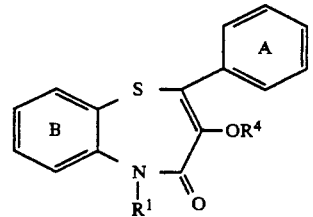

wherein $R^4$ is hydrogen atom or a lower alkanoyl group, and the other symbols are the same as defined above, with a reaction product of an optically active α-amino acid and a metal hydride.

The process of the present invention can equally be applied to any starting compounds [II] wherein Ring A and Ring B have either a substituent or no substituent. The substituent includes, for example, a lower alkyl group, a lower alkoxy group, a halogen atom, etc. More particularly, the substituent for Ring A is, for example, methyl, methoxy and chlorine atom at 4-position thereof, and the substituent for Ring B is, for example, methyl, methoxy and chlorine atom at 8-position thereof.

Moreover, among the starting compounds [II], a compound of the formula [II-b], i.e. a compound of the formula [II] wherein $R^4$ is hydrogen atom, is a tautomer of the compound of the formula [II-a], as shown in the following formula:

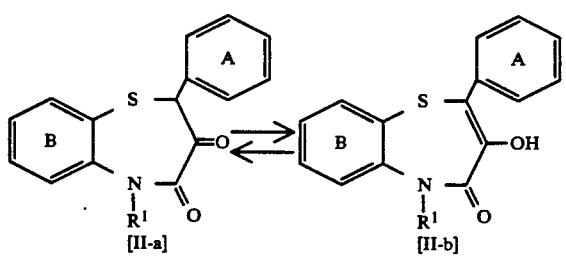

wherein the symbols A, B and $R^1$ are the same as defined above, and these compounds are also included in the starting compounds [II].

The asymmetric reducing agent used in the present invention is obtained by reacting an optically active α-amino acid with a metal hydride. The optically active α-amino acid includes amino acids of the formula [III]:

wherein $R^5$ is a lower alkyl group, said lower alkyl group being more preferably a branched chain alkyl group than a straight chain alkyl group. Preferable optically active α-amino acids are valine, isoleucine, tert-leucine, and the like, particularly tert-leucine is preferable.

Moreover, in either case of using as the optically active α-amino acid an L-amino acid or a D-amino acid, the stereo-configuration of 2- and 3-positions of the obtained optically active cis-3-hydroxy-2-phenyl-2,3-dihydro-1,5-benzothiazepin-4(5H)-one compounds [I] are the opposite. That is, when an L-amino acid is used, there is obtained a (2S,3S)-compound, and when a D-amino acid is used, there is obtained a (2R, 3R)-compound. Accordingly, there can selectively be obtained desired compounds [I] having a desired configuration by selecting L-amino acid or D-amino acid.

The metal hydrides used in the present process are preferably alkali metal borohydrides such as sodium borohydride, lithium borohydride, and the like, and the ratio of the optically active α-amino acid and the metal hydride is in the range of 3:1 to 1:2, preferably in the range of 1.5:1 to 1:1, more preferably 1:1.

The reaction between the metal hydride and optically active α-amino acid is preferably carried out in an appropriate solvent (e.g. tetrahydrofuran, dioxane, monoglyme, diglyme, isopropyl alcohol, tert-butyl alcohol, etc.) under inert gas atmosphere (e.g. nitrogen gas, argon gas, etc.). The reaction is carried out at a temperature from room temperature to a refluxing temperature of the solvent used therein, for example, at a temperature from 25° to 65° C. The reaction product thus obtained may be isolated from the reaction system, but may be used in the asymmetric reduction as it is without isolating.

The asymmetric reduction of the present invention can be carried out by reacting the reaction product of an optically active α-amino acid and a metal hydride obtained above with the starting compound [II].

The amount of the reaction product of an optically active α-amino acid with a metal hydride is not particularly limited, however, it is preferred to use said reaction prouduct in an amount of 1 to 5 moles, preferably 1 to 3 moles, to 1 mole of the starting compound [II].

The asymmetric reduction reaction is usually carried out in an inert solvent which does not disadvantageously affect the reaction. The inert solvent includes, for example, ethers (e.g. diethyl ether, isopropyl ether, tetrahydrofuran, dioxane, monoglyme, diglyme, etc.), alcohols (e.g. isopropyl alcohol, tert-butyl alcohol, etc.) and pyridine.

The reaction can be carried out at a wide range of temperature, i.e. under cooling to with heating, preferably at a temperature from −100° C. to 60° C., more preferably at −50° C. to 15° C. When the reaction product of an optically active α-amino acid and a metal hydride is used in the asymmetric reduction without isolating from the reaction system, the asymmetric reduction can be carried out by adding the starting compound [II] into the reaction system of an optically active α-amino acid and a metal hydride.

Although the desired optically active cis-compounds can be prepared from a racemic starting compound by the process as explained above, the yield and the optical purity of the desired compound can be improved by carrying out the asymmetric reduction in the presence of an acid. The acid includes, for example, mineral acids such as hydrochloric acid, nitric acid, sulfuric acid, hydrogen halides (e.g. hydrogen chloride, hydrogen bromide, etc.), and the like, and organic acids such as straight chain or branched chain fatty acids having 1 to 6 carbon atoms (e.g. formic acid, acetic acid, propionic acid, isobutyric acid, pivalic acid, oxalic acid, etc.), aromatic carboxylic acids (e.g. benzoic acid, etc.), substituted or unsubstituted benzenesulfonic acids (e.g. benzenesulfonic acid, p-toluenesulfonic acid, p-phenolsulfonic acid, etc.), lower alkylsulfonic acids (e.g. methanesulfonic acid, ethanesulfonic acid, etc.), and the like.

The reduction reaction in the presence of an acid can be carried out in the same conditions as described above. The acid is used in an amount of 0.5 to 5 moles, preferably 1 to 2 moles, to 1 mole of the starting compound [II]. The acid may be added into the reaction system either before or after the beginning of the reaction. The acid may be added at once, but preferably be added in several portions.

When the starting compound [II] wherein $R^4$ is a lower alkanoyl group is used in the present asymmetric reduction, said lower alkanoyl group is removed by hydrolysis occurred simultaneously with the asymmetric reduction.

After the reaction is complete, the desired compound [I] is isolated in accordance with a conventional method.

The desired compound [I] thus obtained can be converted into an optically active 1,5-benzothiazepine derivative of the formula [IV]:

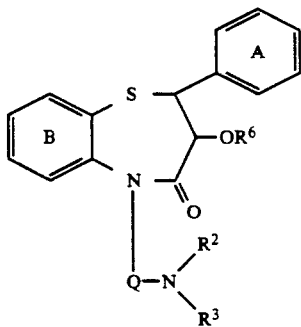

wherein $R^6$ is a lower alkanoyl group or a lower alkoxycarbonylmethyl group, and the other symbols are the same as defined above, according to a conventional method, for example, the method disclosed in Japanese Patent Second Publication (Kokoku) No. 16749/1970, Japanese Patent Second Publication (Kokoku) No. 43785/1971, Japanese Patent Second Publication (Kokoku) No. 813/1972, Japanese Patent Second Publication (Kokoku) No. 18038/1978 or Japanese Patent Second Publication (Kokoku) No. 13994/1988, and further converted into a pharmaceutically acceptable salt thereof, if necessary.

For example, the compound [IV] can be prepared by introducing $R^6$ on the hydroxy group of the compound [I] in a conventional method, and when $R^1$ of the compound [I] is hydrogen atom, followed by condensing the reaction product with an aminoalkyl compound of the formula [V]:

[V]

wherein X is a halogen atom, and the other symbols are the same as defined above.

Alternatively, the compound [IV] can also be prepared by carring out the introduction of $R^6$ and the condensation reaction with the compound [V] in reverse order.

The starting compound [II] used in the present invention can be prepared by the method disclosed in Japanese Patent First Publication (Kokai) No. 25983/1985, or a modified method thereof.

That is, the compound [II] wherein $R^4$ is a lower alkanoyl group can be prepared by oxidizing a 3-hydroxy-2-phenyl-2,3-dihydro-1,5-benzothiazepin-4(5H)-one compound of the formula [VI]:

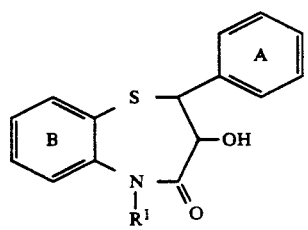

[VI]

wherein the symbols A, B and $R^1$ are the same as defined above (cf. Japanese Patent Second Publication (Kokoku) No. 9383/1970) with dimethylsulfoxide-acetic anhydride, and the starting compound [II]

wherein $R^4$ is hydrogen atom is prepared by treating the product with conc. aqueous ammonia or aqueous sodium hydroxide solution.

The compound [II] wherein $R^1$ is a group of the formula:

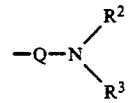

wherein the symbols Q, $R^2$ and $R^3$ are the same as defined above, can be prepared by reacting the compound obtained above with an aminoalkyl compound [V].

Throughout the present claims and specification, the lower alkyl group, lower alkylene group and lower alkoxy group mean alkyl groups, alkylene groups and alkoxy groups having 1 to 6 carbon atoms, preferably 1 to 4 carbon atoms, respectively.

EXAMPLES

The present invention is illustrated in more detail by the following Examples and Reference Examples, but should not be construed to be limited thereto.

The optical purity and the content of the trans-compound are determined by measuring each isomer with high performance liquid chromatography (HPLC) using a column for separating optical isomers, and calculating according to the following equations.

$$\text{Optical purity of the cis-compound (\% e.e.)} = \frac{[(2S, 3S) - (2R, 3R)]}{[(2S, 3S) + (2R, 3R)]} \times 100$$

$$\text{Content of the trans-compound (\%)} = \frac{[(2S, 3R) + (2R, 3S)]}{[\text{Total amount of four isomers}]} \times 100$$

Conditions for *HPLC*:

Column: *CHIRALCEL OD* (manufactured by Daicel Chemical Industries, Ltd.)

Eluent: n-Hexane/ethanol = 85:15 (by volume)

Flow rate: 0.5 ml/min.

Detection: UV 230 nm

Temperature: 35° C.

Example 1

A mixture of L-tert-leucine (393 mg), sodium borohydride (98 mg) and tetrahydrofuran (100 ml) is refluxed under nitrogen atmosphere for three hours. The mixture is cooled to −15° C., and thereto is added 2-(4-methoxyphenyl)-1,5-benzothiazepine-3,4(2H,5H)-dione (599 mg), and the mixture is further stirred at −15° C. for 48 hours. To the reaction solution are added 1N hydrochloric acid (10 ml) and ethyl acetate (20 ml), and the mixture is stirred for 30 minutes. The organic layer is separated, washed with water, dried, and evaporated under reduced pressure to remove the solvent. The resulting residue is dissolved in ethanol (22 ml) with heating, and the mixture is cooled gradually for crystallization. The precipitated crystal is collected by filtration to give (2S,3S)-3-hydroxy-2-(4-methoxyphenyl)-2,3-dihydro-1,5-benzothiazepin-4(5H)-one (376 mg).

Yield: 62.4%.
M.p.: 203°–205° C.
$[\alpha]_D^{25}$: +112° (c=0.5, dimethylformamide).
Optical purity of the cis-compound: 99.1% e.e.
Content of the trans-compound: 0%.

Example 2

A mixture of L-isoleucine (289 mg), sodium borohydride (76 mg) and tetrahydrofuran (15 ml) is refluxed under nitrogen atmosphere for three hours. The mixture is cooled to −20° C., and thereto is added 2-(4-methoxyphenyl)-1,5-benzothiazepine-3,4(2H,5H)-dione (299 mg), and the mixture is stirred at the same temperature for 20 hours. To the reaction solution is added acetic acid (600 mg), and the mixture is stirred for two hours, and then evaporated under reduced pressure to remove the solvent. Water is added to the residue, and the precipitated crystal is collected by filtration, washed with water, and dried to give (2S,3S)-3-hydroxy-2-(4-methoxyphenyl)-2,3-dihydro-1,5-benzothiazepin-4(5H)-one (263 mg).
Yield: 87.4%.
Optical purity of the cis-compound: 61% e.e.
Content of the trans-compound: 12%.

Example 3

Using L-valine (258 mg) instead of L-isoleucine, the same procedures as Example 2 are repeated to give (2S,3S)-3-hydroxy-2-(4-methoxyphenyl)-2,3-dihydro-1,5-benzothiazepin-4(5H)-one (250 mg).
Yield: 83.1%.
Optical purity of the cis-compound: 56% e.e.
Content of the trans-compound: 11%.

Example 4

A mixture of L-tert-leucine (433 mg), lithium borohydride (65.4 mg) and tetrahydrofuran (28 ml) is refluxed under nitrogen atmosphere for one hour. The mixture is cooled to −10° C., and thereto is added 2-(4-methoxyphenyl)-1,5-benzothiazepine-3,4(2H,5H)-dione (299 mg), and the mixture is further stirred at −10° C. for 15 hours. The mixture is evaporated under reduced pressure to remove the solvent, and to the residue is added 1N hydrochloric acid (10 ml). The precipitated crystal is collected by filtration, washed with water, and dried to give (2S,3S)-3-hydroxy-2-(4-methoxyphenyl)-2,3-dihydro-1,5-benzothiazepin-4(5H)-one (282 mg).
Yield: 93.7%.
Optical purity of the cis-compound: 62% e.e.
Content of the trans-compound: 13%.

Example 5

A mixture of L-tert-leucine (525 mg), sodium borohydrie (136 mg) and tetrahydrofuran (27 ml) is refluxed under nitrogen atmosphere for three hours. The mixture is cooled to 0° C., and thereto is added 3-acetoxy-2-(4-methoxyphenyl)-1,5-benzothiazepin-4(5H)-one (683 mg), and the mixture is stirred at 0° C. for five days. To the reaction solution are added 1N hydrochloric acid (10 ml) and ethyl acetate (20 ml), and the mixture is stirred for 30 minutes. The organic layer is separated, washed with water, dried, and evaporated under reduced pressure to remove the solvent. The residue is dissolved in methanol (25 ml) with heating, and cooled gradually for crystallization. The precipitated crystal is collected by filtration to give (2S,3S)-3-hydroxy-2-(4-methoxyphenyl)-2,3-dihydro-1,5,-benzothiazepin-4(5H)-one (270 mg).

Yield: 44.8%.
M.p.: 203°–205° C.
$[\alpha]_D^{25}$: +112.6° (c=0.5, dimethylformamide).
Optical purity of the cis-compound: 99.8% e.e.
Content of the trans-compound: 0%.

Example 6

A mixture of L-tert-leucine (289 mg), sodium borohydride (76 mg) and tetrahydrofuran (15 ml) is refluxed under nitrogen atmosphere for three hours. The mixture is cooled to −15° C., and thereto is added 8-chloro-2-(4-methoxyphenyl)-1,5,-benzothiazepine-3,4(2H,5H)-dione (334 mg). The temperature of the reaction solution is raised to 5° C., and the mixture is stirred at the same temperature for five days. The mixture is evaporated under reduced pressure to remove the solvent, and water (10 ml) is added to the residue. The precipitated crystal is collected by filtration, washed with water, and dried to give (2S,3S)-8-chloro-3-hydroxy-2-(4-methoxyphenyl)-2,3-dihydro-1,5-benzothiazepin-4(5H)-one (284 mg).
Yield: 84.5%.
Optical purity of the cis-compound: 72% e.e.
Content of the trans-compound: 6%.

Example 7

A mixture of D-tert-leucine (289 mg), sodium borohydride (76 mg) and tetrahydrofuran (15 ml) is refluxed under nitrogen atmosphere for three hours. The mixture is cooled to −10° C., and thereto is added a solution of 8-methyl-2-(4-methyl-phenyl)-1,5-benzothiazepine-3,4(2H,5H)-dione (297 mg) in tetrahydrofuran (3 ml). The mixture is stirred at −10° C. for 17 hours, and thereto is added acetic acid (600 mg). The mixture is evaporated under reduced pressure to remove the solvent. To the residue is added water (10 ml), and the precipitated crystal is collected by filtration, washed with water, and dried to give (2R,3R)-3-hydroxy-8-methyl-2-(4-methylphenyl)-2,3-dihydro-1,5-benzothiazepin-4(5H)-one (280 mg).
Yield: 93.6%.
Optical purity of the cis-compound: 77% e.e.
Content of the trans-compound: 9%.
The crystal obtained above is recrystallized from ethanol (8 ml) to give the purified product (125 mg).
M.p.: 212°–214° C.
$[\alpha]_D^{25}$: −129° (c=1, dimethylformamide).
Optical purity of the cis-compound: 99%.
Content of the trans-compound: 0%.

Example 8

2-(4-Methoxyphenyl)-5-[2-(dimethylamino)ethyl]-1,5-benzothiazepine-3,4(2H,5H)-dione is treated in the same manner as in Example 1 to give (2S,3S)-3-hydrox -2-(4-methoxyphenyl)-5-[2-(dimethylamino)ethyl]-2,3-dihydro-1,5-benzothiazepin-4(5H)-one.
Hydrochloride:
M.p.: 225°–227° C. (decomposed).

Example 9

A mixture of L-tert-leucine (721 mg), sodium borohydride (189 mg) and tetrahydrofuran (50 ml) is refluxed under nitrogen atmosphere for three hours. The mixture is cooled to −30° C., and thereto is added 2-(4-methoxyphenyl)-1,5-benzothiazepine-3,4(2H,5H)-dione (997 mg). Each 0.38 ml of 25% acetic acid/tetrahydrofuran solution (1.6 mmole as acetic acid) is added to the reaction solution at 3, 17 and 45 hours after the beginning of the reaction. After the reaction is carried out for 48 hours, the mixture is evaporated to remove the solvent. Water (70 ml) is added to the residue, and the precipitated crystal is collected by filtration, dried, and suspended in isopropyl alcohol (12 ml). The mixture is heated with stirring at 80° C. for three hours, and cooled to 5° C., and then allowed to stand for five hours. The precipitated crystal is collected by filtration to give (2S,3S)-3-hydroxy-2-(4-methoxyphenyl)-2,3-dihydro-1 5-benzothiazepin-4(5H)-one (867 mg).

Yield: 86.4%.
Optical purity of the cis-compound: 99.4% e.e.
Content of the trans-compound: 0.13%.

Examples 10–17

A reducing agent is prepared in the same manner as in Example 9 from a mixture of L-tert-leucine (721 mg), sodium borohydride (189 mg) and tetrahydrofuran (50 ml), and the reaction mixture is cooled to −15° C. To the mixture is added 2-(4-methoxyphenyl)-1,5-benzothiazepine-3,4(2H,5H)-dione (997 mg), and the acid listed in the following Table 1 is added thereto at 30 minutes and 2 hours thereafter (totality: 3.33 mmole), and the reaction is carried out at the same temperature. After confirming by HPLC that the starting compound is completely consumed, the mixture is treated in the same manner as in Example 9 to give (2S,3S)-3-hydroxy-2-(4-methoxyphenyl)-2,3-dihydro-1,5-benzothiazepin-4(5H)-one. The yield, optical purity of the cis-compound and content of the trans-compound are as shown in the following Table 1.

TABLE 1

| Ex. No. | Acid | Reaction Time (hr) | Yield (%) | Optical Purity of Cis-comp (% e.e.) | Content of Trans-comp (%) |
|---|---|---|---|---|---|
| 10 | Formic acid | 4 | 84.4 | 99.6 | 0.02 |
| 11 | Propionic acid | 4 | 83.6 | 99.3 | 0.11 |
| 12 | Isobutyric acid | 5 | 84.5 | 99.0 | 0.22 |
| 13 | Pivalic acid | 5 | 86.2 | 99.6 | 0.07 |
| 14 | Benzoic acid | 4 | 80.5 | 99.5 | 0.13 |
| 15 | p-Toluene-sulfonic acid | 3 | 70.5 | 98.9 | 0.37 |
| 16 | Methane-sulfonic acid | 20 | 75.2 | 99.0 | 0.35 |
| 17 | p-Phenol-sulfonic acid | 70 | 80.5 | 99.3 | 0.22 |

Example 18

A mixture of L-tert-leucine (721 mg), sodium borohydride (189 mg) and tetrahydrofuran (50 ml) is refluxed under nitrogen atmosphere for three hours. The mixture is cooled to −15° C., and thereto is added 8-chloro-2-(4-methoxyphenyl)-1,5-benzothiazepine-3,4(2H,5H)-dione (1113 mg). Each 0.38 ml of 25% acetic acid/tetrahydrofuran solution (1.67 mole as acetic acid) is added thereto at 20 minutes, and 2 hours 20 minutes after the beginning of the reaction, and the reaction solution is stirred at the same temperature for 19 hours. The mixture is evaporated under reduced pressure to remove the solvent, and to the residue is added 1N hydrochloric acid (70 ml). The precipitated crystal is collected by filtration, washed with water, and dried. The collected crystal is suspended in chloroform (50 ml), and the mixture is heated with stirring at 65° C. The mixture is cooled to 5° C., and allowed to stand overnight. The precipitated crystal is collected by filtration, and dried to give (2S,3S)-8-chloro-3-hydroxy-2-(4-methoxyphenyl)-2,3-dihydro-1,5-benzothiazepin-4(5H)-one (896 mg).

Yield: 80.0%.
M.p.: 238°–240° C.
$[\alpha]_D^{25}$: +92.2° (c=0.5, dimethylformamide).
Optical purity of the cis-compound: 99.7% e.e.
Content of the trans-compound: 0.08%.

Example 19

A mixture of D-tert-leucine (721 mg), sodium borohydride (189 mg) and tetrahydrofuran (50 ml) is refluxed under nitrogen atmosphere for three hours. The mixture is cooled to −15° C., and thereto is added a solution of 8-methyl-2-(4-methylphenyl)-1,5-benzothiazepine-3,4(2H, 5H)-dione (991 mg) in tetrahydrofuran (3 ml). Each 0.38 ml of 25% acetic acid/tetrahydrofuran solution (1.67 mmole as acetic acid) is added thereto at 25 minutes, and 2 hours 10 minutes after the beginning of the reaction, and the reaction solution is stirred at the same temperature for 20 hours. The mixture is evaporated under reduced pressure to remove the solvent, and to the residue is added 1N hydrochloric acid (70 ml). The precipitated crystal is collected by filtration, washed with water, and dried. The collected crystal is suspended in isopropyl alcohol (12 ml), and the mixture is heated with stirring at 80° C. for three hours. The mixture is cooled to 5° C., and allowed to stand for five hours. The precipitated crystal is collected by filtration, washed with cold isopropyl alcohol, and dried to give (2R,3R)-3-hydroxy-8-methyl-2-(4-methylphenyl)-2,3-dihydro-1,5-benzothiazepin-4(5H)-one (804 mg).

Yield: 80.5%.
M.p.: 212°–214° C.
$[\alpha]_D^{25}$: −129.9° (c=1, dimethylformamide).
Optical purity of the cis-compound: 98.7% e.e.
Content of the trans-compound: 0.1%.

Example 20

A mixture of L-tert-leucine (721 mg), sodium borohydride (189 mg) and tetrahydrofuran (25 ml) is refluxed under nitrogen atmosphere for three hours. The mixture is cooled to room temperature, and thereto is added tetrahydrofuran (25 ml). The mixture is cooled to −30° C., and thereto is added 2-(4-methoxyphenyl)-1,5-benzothiazepine-3,4(2H,5H)-dione (997 mg). Each 139 μl of conc. hydrochloric acid (1.67 mmole as hydrogen chloride) is added at 1, 3, 5 and 22 hours after the beginning of the reaction, and the reaction is carried out for 45 hours. After confirming by HPLC that the starting compound is completely consumed, the mixture is evaporated under reduced pressure to remove the solvent, and water (70 ml) is added to the residue. The mixture is stirred at room temperature for one hour, and the precipitated crystal is collected by filtration and dried. The resulting residue is suspended in isopropyl alcohol (13 ml), and the mixture is refluxed for one hour. The mixture is cooled to 5° C., and allowed to stand overnight. The precipitated crystal is collected by filtration, and washed with cold isopropyl alcohol, and dried to give (2S,3S)-3-hydroxy-2-(4-methoxyphenyl)-2,3-dihydro-1,5-benzothiazepin-4(5H)-one (842 mg).

Yield: 83.9%.
Optical purity of the cis-compound: More than 99.9% e.e.
Content of the trans-compound: 0.13%.

PREPARATION OF THE STARTING COMPOUNDS

Reference Example 1

(1) A mixture of 8-chloro-2,3-dihydro-3-hydroxy-2-(4-methoxyphenyl)-1,5-benzothiazepin-4(5H)-one (36.0 g), acetic anhydride (50 ml), dimethylsulfoxide (100 ml), pyridine (3 ml) and toluene (100 ml) is stirred at room temperature for 3 days. Water is added to the mixture, and the mixture is extracted with ethyl acetate, and the extract is washed with water, and dried. The resultant is evaporated to remove the solvent, and diethyl ether is added to the residue. The precipitated crystal is collected by filtration to give 3-acetoxy-8-chloro-2-(4-methoxyphenyl)-1,5-benzothiazepin-4(5H)-one (24.5 g).
Yield: 60.8%.
M.p.: 236°–238° C.

(2) This product (7.52 g) is dissolved in a mixture of 2N aqueous sodium hydroxide solution (25 ml), methanol (60 ml) and dimethylformamide (100 ml), and the mixture is stirred overnight. To the mixture is added 2N hydrochloric acid to adjust the pH value of the mixture to pH 3. The mixture is extracted with ethyl acetate, and the extract is washed with water, and dried. The residue is evaporated to remove the solvent, and diethyl ether is added to the residue. The precipitated crystal is collected by filtration to give 8-chloro-2-(4-methoxyphenyl)-1,5 -benzothiazepine-3,4(2H,5H)-dione (6.38 g).
Yield: 95.6%.
M.p.: 168°–169° C.

Reference Example 2

(1) A mixture of 2,3-dihydro-3-hydroxy-8-methyl-2-(4-methylphenyl)-1,5-benzothiazepin-4(5H)-one (30.0 g), acetic anhydride (50 ml), dimethylsulfoxide (100 ml), pyridine (3 ml) and toluene (100 ml) is stirred at room temperature for 4 days, and the mixture is treated in the same manner as in Reference Example 1-(1) to give 3-acetoxy-8-methyl-2-(4-methylphenyl)-1,5-benzothiazepin-4(5H)-one (24.0 g).
Yield: 70.6%.
M.p.: 233°–235° C.

(2) This product (5.1 g) is dissolved in a mixture of 2N aqueous sodium hydroxide solution (15 ml) and methanol (15 ml), and the mixture is stirred for two hours. The mixture is treated in the same manner as in Reference Example 1-(2) to give 8-methyl-2-(4-methylphenyl)-1,5-benzothiazepine-3,4(2H,5H)-dione (4.2 g).
Yield: 94.0%.
M.p.: 141.5°–144° C.

EFFECTS OF THE INVENTION

According to the present invention, the desired (2S,3S)- or (2R,3R)-3-hydroxy-2-phenyl-1,5-benzothiazepin-4(5H)-one compounds, which are very important as an intermediate for preparing medicines, can be obtained in high optical purity and high yield from racemic starting compounds by using as a reducing agent a reaction product of an industrially available optically active α-amino acid and a metal hydride, and hence, the process of the present invention is industrially very useful.

What is claimed is:

1. A process for preparing an optically active cis-3-hydroxy-2-phenyl-2,3-dihydro-1,5-benzothiazepine compound of the formula (I):

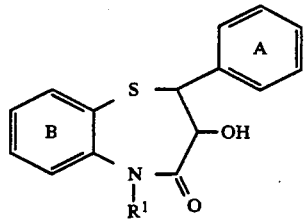

wherein Ring A and Ring B are each an unsubstituted benzene ring or a benzene ring substituted by a substituent selected from the group consisting of a lower alkyl group, a lower alkoxy group and a halogen atom, $R_1$ is a hydrogen atom or a group of the formula:

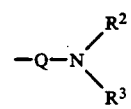

wherein $R_2$ and $R_3$ are the same or different and a lower alkyl group or a lower alkoxy-substituted-phenyl lower alkyl group, and Q is a lower alkylene group, which process comprises subjecting a 2-phenyl-1,5-benzothiazepin-4(5H)-one compound of the formula (II):

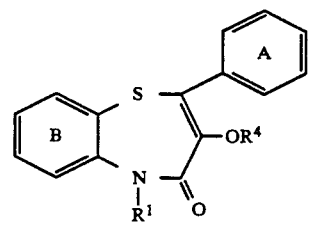

wherein $R^4$ is a hydrogen atom or a lower alkanoyl group, and $R^1$, Ring A and Ring B are the same as defined above, to asymmetric reduction with a reaction product of an optically active α-amino acid and a metal hydride.

2. A process for preparing an optically active cis-3-hydroxy-2-phenyl-2,3-dihydro-1,5-benzothiazepin-4(5H)-one compound of the formula (I):

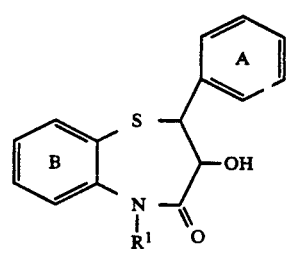

wherein Ring A and Ring B are each an unsubstituted benzene ring or a benzene ring substituted by a substituent selected from the group consisting of a lower alkyl group, a lower alkoxy group and a halogen atom, and $R_1$ is a hydrogen atom or a group of the formula:

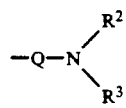

wherein $R_2$ and $R_3$ are the same or different and a lower alkyl group or a lower alkoxy-substituted phenyl-lower alkyl group, and Q is a lower alkylene group, which process comprises subjecting a 2-phenyl-1,5-benzothiazepine-3,4(2H,5H)-dione compound of the formula (II-a):

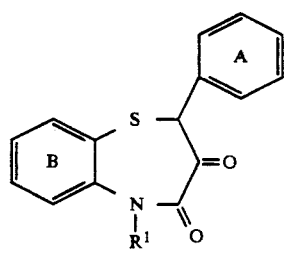

wherein Ring A, Ring B and $R^1$ are the same as defined above, to asymmetric reduction with a reaction product of an optically active α-amino acid and a metal hydride.

3. The process according to any one of claims 1 and 2, wherein the asymmetric reduction is carried out in the presence of an acid.

4. The process according to any one of claims 1 to 2, wherein Ring A and Ring B are a benzene ring substituted by a substituent selected from a group consisting of a lower alkyl group, a lower alkoxy group and a halogen atom.

5. The process according to any one of claims 1 to 2, wherein the optically active α-amino acid is an amino acid of the formula [III]:

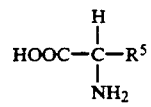

wherein $R^5$ is a lower alkyl group.

6. The process according to any one of claims 1 to 2, wherein the optically active α-amino acid is an amino acid selected from the group consisting of valine, isoleucine and tert-leucine.

7. The process according to any one of claims 1 to 2, wherein the metal hydride is an alkali metal borohydride.

8. A process for preparing an optically active 1,5-benzothiazepine derivative of the formula (IV):

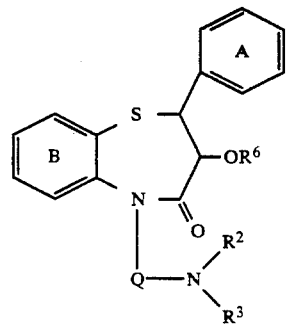

wherein Ring A and Ring B are each an unsubstituted benzene ring or a benzene ring substituted by a substituent selected from the group consisting of a lower alkyl group, a lower alkoxy group and a halogen atom, $R^2$ and $R^3$ are the same or different and a lower alkyl group or a lower alkoxy-substituted phenyl-lower alkyl group, $R^6$ is a lower alkanoyl group or a lower alkoxycarbonylmethyl group, and Q is a lower alkylene group, or a pharmaceutically acceptable salt thereof, which comprises converting the compound (I) obtained in any one of claims 1 to 2 into the optically active 1,5-benzothiazepine compound (IV) by a conventional method.

9. The process according to claim 8, wherein said optically active 1,5-benzothiazepine compound (IV) is converted into a pharmaceutically acceptable salt thereof.

* * * * *